US009867796B2

(12) United States Patent
Van Norren et al.

(10) Patent No.: US 9,867,796 B2
(45) Date of Patent: Jan. 16, 2018

(54) COMBINATION OF A LEUCINE SOURCE AND AN OMEGA-3 UNSATURATED FATTY ACID SOURCE FOR USE IN THE TREATMENT OF HYPERCALCAEMIA (71) Applicant: N.V. Nutricia, Zoetermeer (NL)

(72) Inventors: Klaske Van Norren, Renkum (NL); Joyce Faber, Goor (NL); Adrianus Lambertus Bertholdus Van Helvoort, Wageningen (NL); Robert Johan Joseph Hageman, Wageningen (NL)

(73) Assignee: N.V. Nutricia (NL)

( * ) Notice: Subject to any disclaimer, the term of this patent is extended or adjusted under 35 U.S.C. 154(b) by 0 days.

(21) Appl. No.: 14/341,106

(22) Filed: Jul. 25, 2014

(65) Prior Publication Data
US 2015/0018277 A1    Jan. 15, 2015

Related U.S. Application Data (62) Division of application No. 13/322,730, filed as application No. PCT/NL2010/050319 on May 27, 2010, now abandoned.

(30) Foreign Application Priority Data

May 27, 2009 (WO) ................ PCT/NL2009/050297

(51) Int. Cl.
*A61K 38/00* (2006.01)
*A61P 7/00* (2006.01)
*A61K 31/202* (2006.01)
*A61K 31/198* (2006.01)
*A61K 31/715* (2006.01)
*A61K 45/06* (2006.01)
*A61K 31/702* (2006.01)
*A61K 38/02* (2006.01)
*A23L 33/12* (2016.01)
*A23L 33/17* (2016.01)
*A23L 33/175* (2016.01)

(52) U.S. Cl.
CPC ............ *A61K 31/202* (2013.01); *A23L 33/12* (2016.08); *A23L 33/17* (2016.08); *A23L 33/175* (2016.08); *A61K 31/198* (2013.01); *A61K 31/702* (2013.01); *A61K 31/715* (2013.01); *A61K 38/02* (2013.01); *A61K 45/06* (2013.01); *A23V 2002/00* (2013.01)

(58) Field of Classification Search
CPC .............. A61K 2300/00; A61K 31/198; A61K 31/702; A23L 33/12; A23L 33/17; A23L 33/175
See application file for complete search history.

(56) References Cited

U.S. PATENT DOCUMENTS

| | | |
|---|---|---|
| 2004/0171692 A1 | 9/2004 | Andrew et al. |
| 2006/0159746 A1 | 7/2006 | Troup et al. |
| 2007/0031537 A1 | 2/2007 | Secretin |
| 2008/0200425 A1 | 8/2008 | Kurtz |
| 2009/0011078 A1 | 1/2009 | Johnson |

FOREIGN PATENT DOCUMENTS

| | | | |
|---|---|---|---|
| CN | 1684676 A | 10/2005 | |
| CN | 101314031 A | 12/2008 | |
| EP | 0543310 A2 | 5/1993 | |
| EP | 2025248 A1 | 2/2009 | |
| JP | H05-140063 A | 6/1993 | |
| JP | H05-178758 A | 7/1993 | |
| NZ | WO 2008147228 A1 * | 12/2008 | ............. A61K 31/19 |
| WO | 2004026294 A1 | 4/2004 | |
| WO | 2009/000877 A1 | 12/2008 | |
| WO | 2010/002242 A1 | 1/2010 | |
| WO | 2010/002257 A1 | 1/2010 | |

OTHER PUBLICATIONS

ScienceNow, American Institute for Cancer Research (AICR) ScienceNow, fall 2006, vol. 18, accessed online on Dec. 19, 2015 at http://preventcancer.aicr.org/site/News2?page=NewsArticle&id=11325&news_iv_ctrl=0&abbr=res_.*
Morris, Flax—A Health and Nutrition Primer | Flax Council of Canada, 2007.*
1stvitality, Health Benefits of Organic High Lignan Flax Seed Oil, archived on 2006, accessed online on Dec. 19, 2015 at: https://web.archive.org/web/20060211191541/http://www.1stvitality.co.uk/pdfs/INFO_GB.pdf.*
Norton, https://www.bodybuilding.com/fun/the-case-for-casein.html, accessed on Apr. 3, 2017.*
Liu, Oncolink, Penn Medicine, Nov. 1, 2001, accessed online on 2017.*
Decision Guide, Cancer Treatment Centers of America®, Mar. 1, 2002.*
Fact Sheet New Drug Development Process, California Biomedical Research Association, Jun. 25, 2008.*
Högström, et al., "n-3 Fatty Acids are Positively Associated with Peak Bone Mineral Density and Bone Accrual in Healthy Men: the NO2 Study 1-3," Am J. Clin Nutr, 2007, 85:803-7.
Salari, et al., "A Systematic Review of the Impact of n-3 Fatty Acids in Bone Health and Osteoporosis," Med Sci Monit, 2008, 14(3): RA37-44.
Ordman, Age, 2008, 30, 201-208, published online on Apr. 3, 2008.
International Search Report dated Mar. 1, 2011, issued from corresponding PCT/NL2010/050319.
Entsiklopedicheskii slovar meditdinskikh terminov [Dictionary of medical terms], Ed. V.I. Pokrovskii, Moscow, "Meditsina", 2001, p. 46.
Office Action issued for corresponding Russian Patent Application No. 2011152873, dated Dec. 9, 2013.

(Continued)

*Primary Examiner* — Kaipeen Yang
(74) *Attorney, Agent, or Firm* — Banner & Witcoff, Ltd.

(57) ABSTRACT

The present invention relates to a combination of a leucine source and at least one unsaturated fatty acid source for prophylactic or therapeutic treatment of hypercalcaemia. The invention further relates to a combination of a leucine source and at least one unsaturated fatty acid source for reducing or avoiding a reduction in bone mineral density in a subject or for in vivo regulating of the blood plasma calcium homeostasis.

31 Claims, 7 Drawing Sheets

(56) References Cited

OTHER PUBLICATIONS

European Search Report issued in corresponding European Application No. 15184059.2, dated Dec. 11, 2015.
Office Action issued for corresponding Chinese Patent Application No. 201410488463.7, dated Feb. 3, 2016.
Tashjian, Armen H., et al., Dietary Menhaden Oil Lowers Plaxma Prostaglandins and Calcium in Mice Bearing the Prostaglandin-Producing HSDM, Fibrosarcoma, Journal of Clinical Investigation, vol. 74, pp. 2042-2048, Dec. 1984.
Fernandes, Gabriel, et al., Protective role of n-3 lipids and soy protein in osteoporosis, Prostaglandins, Leukotrienes and Essential Fatty Acids, vol. 68, pp. 361-372, 2003.
Purasiri, P. et al., Modulation of cytokine production in vivo by dietary essential fatty acids in patients with colorectal cancer, Clinical Science, vol. 87, pp. 711-717, 1994.
Communication in corresponding EP Patent 2435039 dated Jun. 10, 2016.
Wikipedia, "Soybean Oil", https://en.wikipedia.org/wiki/Soybean_oil, downloaded: May 25, 2016.

\* cited by examiner

COMBINATION OF A LEUCINE SOURCE AND AN OMEGA-3 UNSATURATED FATTY ACID SOURCE FOR USE IN THE TREATMENT OF HYPERCALCAEMIA

RELATED APPLICATIONS

This application is a divisional of U.S. application Ser. No. 13/322,730 filed Nov. 28, 2011, which is a continuation-in-part of International application PCT/NL2010/050319, filed May 27, 2010, which claims the benefit of International application PCT/NL2009/050297, filed May 27, 2009, all of which are hereby incorporated herein by reference in their entireties.

The invention is directed to a specific combination of at least two components for treatment of hypercalcaemia, for reducing or avoiding a reduction in bone mineral density in a subject, or for in vivo regulating of the blood plasma calcium homeostasis.

Calcium plays a vital role in many different physiological functions, especially in the translation of excitation stimuli of neuro- and muscular tissues. Further, calcium is involved in signal transduction routes that e.g. can result in changes in hormonal balances (e.g. in cholecystokinin balance). In healthy individuals the concentration of plasma calcium homeostasis is tightly regulated and kept within narrow limits (between 8.4 and 10.2 mg/dL or 2.1 and 2.6 mM) by parathyroid hormone, vitamine D and calcitonin (see "Strassman et al. (1993). Mechanisms of paraneoplastic syndromes of colon-26: involvement of interleukin 6 in hypercalcaemia. Cytokine, 5, 463-8").

Hypercalcemia is defined at plasma calcium levels above 2.8 mmol/L in men or above 2.5 mmol/L in women (Bradley & Hoskin, 2006, Hypercalcaemia in head and neck squamous cell carcinoma. Curr Opin Otolaryngol Head Neck Surg., 14, 51-4).

The symptoms observed in hypercalcaemic patients are related to the physiological and neuro/muscular function of calcium and include: fatigue, nausea, vomiting, constipation, mental decline, renal failure, coma, head ache and altered sensorium. Hypercalcaemia most commonly occurs in association with malignant disorders or primary hyperparathyroidism. A considerable percentage of patients with neoplasms, e.g. lung cancer, breast cancer, kidney cancer, lymphoblastic leukaemia, multiple myeloma cancer or head and neck cancer develop hypercalcaemia.

There are at least two different forms of malignancy associated hypercalcaemia. One is associated with dissolving of bone by invading metastases (Berenson, J. R., Rajdev, L. & Broder, M. (2006). Managing bone complications of solid tumours. Cancer Biol Ther., 5, 1086-9. Epub 2006 Sep. 20.). The other form has been associated with several different mechanisms leading to increased breakdown of bone. One of these mechanisms includes the secretion of PTH related hormone (PTHrH) by the tumour, which can lead to increased bone demineralisation and or increased renal reapsorbtion of calcium, due to cross reaction of PTHrH with the PTH receptor. But also inflammatory cytokines have been reported to be involved in the induction of hypercalcaemia (Mitnick, M., Isales, C., Paliwal, I. & Insogna, K. (1992). Parathyroid hormone-related protein stimulates prostaglandin E2 release from human osteoblast-like cells: modulating effect of peptide length. *J Bone Miner Res.*, 7, 887-96).

Calcium levels in blood have been reported to be an independent predictor of quality of life in multiple myeloma patients. Moreover, a correlation between calcium levels and physical functioning scores of these patients has been reported. Apart from fatigue, other quality of life parameters have been reported to be correlated to calcium levels. A significant relationship between calcium and appetite loss at diagnosis was reported. Moreover, serum calcium was related to nausea and vomiting. It was mentioned as a predictor of pain and a relation with cognitive function was suggested.

Serum calcium is an independent predictor of quality of life in multiple myeloma (*Eur J Haematol.*, 78, 29-34. Epub 2006 Oct. 13.). The calcium level in blood is an independent predictor of quality of life in multiple myeloma. In this study 32% of the 686 patients were hypercalcaemic. In addition it was reported that there was a linear component in the correlation of calcium with quality of life scores, fatigue and physical functioning. These findings indicate that also mild elevations of calcium levels within levels that are accepted as normal variations, might contribute to cancer-related fatigue and cancer-related reductions in physical performance.

It has been observed that even within normal ranges of calcium, serum calcium was associated with insulin resistance and that small elevations within normal range of calcium levels might contribute to the development of diabetes. Insulin resistance is a major problem in different kind of chronic diseases like COPD, HIV, Alzheimer, cancer, renal failure, heart failure, and a disease state characterized by a high plasma and/or serum level of pro-inflammatory cytokines Further, the treatment of patients suffering from a disorder different from hypercalcaemia with medication can cause or worsen fatigue, physical malfunctioning or mental malfunctioning. For instance, anthracyclines are widely used to treat solid tumours and haematological malignancies. Patients suffering from these types of cancers are also at risk of developing hypercalcaemia (Higdon, M. L. & Higdon, J. A. (2006). Treatment of oncologic emergencies. *Am Fam Physician.*, 74, 1873-80). Direct effects of the anthracycline doxorubicin on calcium homeostasis in skeletal muscle might contribute to chemotherapy induced fatigue (van Norren, K. et al. (2009), "Direct effects of doxorubicin on skeletal muscle contribute to fatigue" *Br J Cancer.*, 100, 311-4.). Therefore, the patient group suffering from solid tumours and haematological malignancies and treated with anthracyclines or other another form of chemotherapy, might even be more susceptible to sustained exhaustion as a result of impaired muscle function due to elevated calcium levels. Also irradiation can increase or initiate bone breakdown.

WO 01/60355 relates to the use of compounds that are an activator of or a ligand to peroxisome proliferator-activated receptors for the treatment or prophylaxis of bone disease, e.g. a cancer which results in hypercalcaemia. Amongst said compounds a number of unsaturated fatty acids are mentioned, which apparently may contribute to bone anabolic activity. However, no experimental results are shown specifically directed at the treatment of subjects suffering from hypercalcaemia. In particular, no effect of unsaturated fatty acids on plasma calcium levels is shown or suggested.

The inventors have found that the use of unsaturated fatty acid (in a vegetable oil, a fish oil or a mixture thereof) alone may be insufficient to have a significant effect on plasma calcium levels in tumour bearing mice, see the examples below. Further, no significant effect of unsaturated fatty acid (in a vegetable oil, a fish oil or a mixture thereof) alone on a reduction of bone catabolism (resulting in an increased bone density) was observed in the mice.

It is an objective of the invention to provide a novel means to treat hypercalcaemia, in particular a means that would allow reduction of the plasma calcium level in a subject suffering from hypercalcaemia or maintainance of the blood plasma level at a normal level, in a patient having a risk of developing hypercalcaemia and/or that would allow avoiding or reducing bone density loss associated with hypercalcaemia and/or alleviating one or more other symptoms associated with hypercalcaemia, e.g. fatigue, reduced muscle function.

One or more further objectives underlying the present disclosure will be apparent from the description below.

It has now been found that a combination of a specific unsaturated fatty acid and a specific other component is useful for prophylactically or thereapeutically treating hypercalcaemia.

Accordingly, the present invention relates to a combination of a leucine source and at least one ω-3 polyunsaturated fatty acid, for prophylactic or therapeutic treatment of hypercalcaemia.

Further, the invention relates to a combination of a leucine source and at least one ω-3 polyunsaturated fatty acid, for reducing a loss in bone mineral density or avoiding a reduction in bone mineral density in a subject.

Further, the invention relates to a combination of a leucine source and at least one ω-3 polyunsaturated fatty acid, for in vivo regulating of the blood plasma calcium homeostasis.

Further, the invention relates to a combination of a leucine source and at least one ω-3 polyunsaturated fatty acid source for improving appetite and/or for increasing total voluntary food intake per day and/or for reducing nausea and/or for reducing vomiting urges. Loss of appetite, nausea and urges to vomit are symptoms that may be associated with abnormal blood plasma calcium levels.

Further, the invention relates to a nutritional composition, a pharmaceutical composition or a nutraceutical composition comprising a combination of leucine and at least one ω-3 polyunsaturated fatty acid for prophylactic or therapeutic treatment of hypercalcaemia, for reducing a loss in bone mineral density or avoiding a reduction in bone mineral density in a subject, for in vivo regulating of the blood plasma calcium homeostasis, for improving appetite, for reducing nausea or reducing vomiting urges.

In a specific embodiment, the combination or composition of the invention is for prophylactic or therapeutic treatment of excessive calcium release from bone and/or skeletal muscle; and/or excessive calcium accumulation due to kidney failure or hyperparathyroidism. This accumulation or excessive release might be associated with fatigue, tiredness, loss of initiative, loss of muscle function, heart arrhythmia, osteopenia, osteoporoses, bone diseases, nausea, vomiting or loss of appetite, and can result in polyuria, oligouria and kidney damage.

It has been found that a combination of a leucine source and a ω-3 polyunsaturated fatty acid, has a beneficial effect on bone mineral density and/or on calcium levels in blood plasma in subjects suffering from hypercalcaemia. It is noted that a treatment with a combination of a leucine source and a ω-3 polyunsaturated fatty acid source in accordance with the invention the calcium level in blood plasma does not have to lead to a reduction to a normal calcium level, in all circumstances. For instance, the calcium levels may be brought to or maintained at a normal vale or slightly elevated level (up to about 2.8 mM in humans), whereby the occurrence of an a medical emergency due to severe hypercalcaemia (calcium level in blood plasma exceeding 3.75 mM), which may result in coma or cardiac arrest, may be avoided.

Further, also in case during or after treatment the calcium level is not fully normalised by treatment with a combination or composition in accordance with the invention, the subject may benefit from one or more advantageous effects, such as improved muscle function (e.g. higher maximum force), less fatigue, increased physical activity, reduced cachexia, and/or addressing one or more of the symptoms like nausea, vomiting, constipation, mental decline, renal failure, head ache, altered sensorium, loss of appetite.

The term "or" as used herein means "and/or" unless specified other wise.

The term "a" or "an" as used herein means "at least one" unless specified other wise.

When referring to a 'noun' (e.g. a compound, an additive etc.) in singular, the plural is meant to be included, unless specified otherwise.

When referring to "a combination of a leucine source and an ω-3 polyunsaturated fatty acid source" for a specific purpose it is meant that both leucine (provided by that leucine source) and ω-3 polyunsaturated fatty acid (provided by that ω-3 polyunsaturated fatty acid source) are intended to be used for that purpose in combination. The leucine source and ω-3 polyunsaturated fatty acid source may be administered together in a single formulation (such as a food, a nutraceutical or a pharmaceutical composition), administered simultaneously in separate formulations or subsequently in separate formulations. If administered subsequently, the formulations are usually administered shortly after each other, i.e. in case of oral/enteral administration the later administered formulation is then usually administered before the earlier administered formulation has been absorbed by the body.

In principle, a combination or composition according to the invention may be used for treatment of any vertebrate, in particular any mammal, more in particular any human. The subject may be male of female. The subject may be a child, an adolescent or an adult. Hypercalcaemia can be diagnosed in a manner known per se, by determining the blood plasma calcium level. As indicated above, a human male is considered to be hypercalcaemic at plasma calcium levels above 2.8 mmol/L, a human female is considered to be hypercalcaemic at plasma at calcium levels above 2.5 mmol/L.

In a specific embodiment, the combination or composition is for treatment of an elderly person. In this respect, it is submitted that in the context of this application, an elderly person is a human of the age of 50 or more, in particular of the age of 55 or more, more in particular of the age of 60 or more, more in particular of the age of 65 or more. This rather broad definition takes into account the fact that the average age varies between different populations, on different continents, etc. Most developed world countries have accepted the chronological age of 65 years as a definition of 'elderly' or older person (associated with the age at which one may begin to receive pension benefits), but like many westernized concepts, this does not adapt well to e.g. the situation in Africa. At the moment, there is no United Nations (UN) standard numerical criterion, but the UN agreed cut-off is 60+ years to refer to the older population in Western world. The more traditional African definitions of an elder or 'elderly' person correlate with the chronological ages of 50 to 65 years, depending on the setting, the region and the country.

In principle, any form of hypercalcaemia may be treated in accordance with the invention, in particular hypercalcaemia at least partially caused by excessive skeletal calcium release and/or by decreased renal calcium excretion.

The subject to be treated with a combination of composition according to the invention may suffer from hypercalcaemia (in which case the treatment may be referred to as 'thereapeutic'), or the subject may be treated in order to avoid developing a hypercalcaemic state or at least reduce one or more symptoms resulting from hypercalcaemia, should hypercalcaemia develop after all. A prophylactic treatment may in particular be useful for any subject having a serious risk of developing hypercalcemia. A serious risk exists for subjects suffering from a disorder or condition, wherein hypercalcaemia is (statistically) known to develop in considerable cases.

In particular, the subject to be treated prophylactically or therapeutically may be selected from the group of subjects suffering from a cancer. It is contemplated that in particular subjects also treated with chemotherapy or radiotherapy, e.g. with an anthracycline, may also benefit from a treatment with a combination of composition of the invention.

The cancer may in particular be selected from the group of neoplasms. More in particular the cancer may be selected from lung cancer, breast cancer, kidney cancer, multiple myeloma cancer, and head and neck cancer. Further, in particular subjects suffering from a hematologic malignancy (multiple myeloma, lymphoma, leukaemia), vitamin-D related disorders that can result in hypercalcaemia (hypervitaminosis D), disorders/conditions related to high bone-turnover rates (hyperthyroidism, prolonged immobilisation, Paget's disease of the bone), renal failure, intoxication with specific substances that may result in hypercalcaemia (e.g. aluminium, intoxication, vitamin A intoxication) may benefit from a prophylactic or therapeutic treatment in accordance with the invention.

In principle any food-grade lipid or mixture of lipids comprising free ω-3 polyunsaturated fatty acid or fatty-acid derivative (including tri-, di-, and monoglycerides and phospholipids) may serve as ω-3 polyunsaturated fatty acid source. When referred herein to fatty acids, this is meant to include the corresponding fatty acid residues in derivatives thereof that provide the fatty acid when digested, such as triglycerides, diglycerides, monoglycerides and phospholipids of said fatty acids.

The ω-3 polyunsaturated fatty acid for a treatment in accordance with the invention is usually selected from the group of long chain ω-3 polyunsaturated fatty acids. The term "long chain" is used herein for ω-3 polyunsaturated fatty acids having at least 18 carbon atoms, in particular for C18-C26 ω-3 polyunsaturated fatty acids.

Preferred ω-3 polyunsaturated fatty acids in particular include eicosapentaenoic acid (EPA), docosahexaenoic acid (DHA), eicosatetraenoic acid (ETA) and docosapentaenoic acid (DPA). Of these, in particular good results have been achieved with a mixture comprising EPA and DHA. Further examples of ω-3 polyunsaturated fatty acid, for use in accordance with the invention, include alpha-linolenic acid and stearidonic acid.

The ω-3 polyunsaturated fatty acid content, in particular the long chain ω-3 polyunsaturated fatty acid, in a composition of the invention preferably is at least 15 g/kg, in particular at least 20 g/kg, based on total weight of macronutrients of the composition. The ω-3 polyunsaturated fatty acid content, in particular the long chain ω-3 polyunsaturated fatty acid, is usually 50 g/kg or less, in particular 40 g/kg or less, based on total weight of macronutrients of the composition. When referred in this disclosure to the "total weight of macronutrients" the total content of proteineous matter, lipids, carbohydrate plus dietary fibres is meant.

A composition according to the invention may further comprise one or more other fatty acids in addition to the ω-3 polyunsaturated fatty acid, which other fatty acid(s) which may be saturated or unsaturated.

Usually, the composition comprises 300 g/kg or less total fatty acids, in particular 200 g/kg or less, more in particular 180 g/kg or less, based on total weight of macronutrients of the composition.

The total fatty acid content of a composition according to the invention may in particular be at least 50 g/kg, based on total weight of macronutrients of the composition, more in particular at least 100 g/kg based on total weight of macronucrients of the composition.

The total ω-3 polyunsaturated fatty acid content, in particular the long chain ω-3 polyunsaturated fatty acid, usually is at least 12 wt. %, preferably at least 15 wt. %, in particular at least 20 wt. %, more in particular at least 24 wt. %, based on total fatty acids. In practice, the ω-3 polyunsaturated fatty acid content, in particular the long chain ω-3 polyunsaturated fatty acid, usually is 75 wt. % or less, in particular 50 wt. % or less, more in particular 40 wt. % or less, based on total fatty acids.

In particular, good results have been achieved with a combination of leucine and a mixture of PUFA's, which mixture comprises DHA and EPA, the DHA and EPA preferably providing at least 5 wt. %, in particular at least 14 wt. % of total fatty acids. The weight to weight ratio DHA to EPA, may in particular be in the range of 1:9 to 9:1, more in particular in the range of 2:8 to 8:2, or in the range of 3:7 1:1.

The weight to weight ratio DPA to EPA, may in particular be in the range of 1:20 to 1:4, more in particular in the range of 1: 15 to 1:8.

As sources for the fatty acid(s) various oils are commercially available, e.g. various oils from cereals and other plants. Marine oil, such as fish oil, oil from plankton or oil from algae is particular suitable as a source for ω-3 polyunsaturated fatty acids. In a specific embodiment at least 70 wt. % of the ω3-polyunsaturated fatty acid content originates from marine oil, in particular from fish oil or from oil from algae.

In terms of a daily dosage (for an adult subject, e.g. weighing 70 kg, in particular an adult human) the combination or composition is usually administered to provide a daily ω3-polyunsaturated long chain fatty acid dosage, in particular a long chain ω-3 polyunsaturated fatty acid dosage, of at least 3.5 g/day. The upper limit may be determined based on a maximum recommended daily dosage, according to general dietary principles. In particular, said dosage may be 25 g/day or less or 20 g/day or less.

In particular for a combination or composition that is for oral administration, e.g. a liquid nutritional composition, such as a sip feed (i.e. a liquid food product that can be ingested by drinking), said daily ω-3 polyunsaturated fatty acid dosage, is preferably in the range of 3.5 to 6 g/day.

In particular for a combination or composition that is for tube feeding said daily ω-3 polyunsaturated fatty acid dosage is preferably in the range of 10 to 20 g/day.

Leucine generally forms part of a group of molecules that may be referred to herein as 'proteinaceous matter'. Proteinaceous matter is formed by moieties formed from amino acids. The term amino acids as used herein includes amino-acid residues (e.g. in peptides). In particular the term 'proteinaceous matter' includes free amino acids, amino acid salts, amino acid esters, the amino acid residues bound to conjugating molecules and peptides, including proteins. Likewise, when reference is made to a specific amino acid, e.g. leucine, this is meant to include the specific amino acid (residues) present as a salt, in a bound form, as well as the free specific amino acid.

Thus, as used herein, the term leucine source is used for any compound that provides leucine when properly administered to the body, in particular that provides leucine, upon digestion of the source. The leucine source may in particular comprise at least one of the following compounds: leucine in the form of a free acid (including its zwitter ionic state); leucine salts; peptides comprising one or more leucine residues; proteins comprising one or more leucine residues; and conjugates of leucine with a conjugating compound other than an amino acid, a protein, or a peptide, which conjugate is capable of being split into the free amino acid (or salt thereof), preferably in the gut or stomach or after absorption in the enterocytes or liver. In principle, leucine may be present as a D-isomer or an L-isomer, preferably the leucine is L-leucine Hereinafter, unless specified otherwise, when referred to leucine, leucine in any form is meant, i.e. including not only the free amino acid (acid/salt) but also leucine in any bound form.

With a peptide is meant a combination of two or more amino acids, connected via one or more peptidic bonds. When incorporated in a peptide, amino acids are named amino-acid residues. Peptides include oligopeptides and polypeptides, including proteins.

With a polypeptide is meant a peptide chain comprising 14 or more amino-acid residues. With an oligopeptide is meant a peptide chain comprising 2 to 13 amino-acid residues.

Chiral amino acids present in a combination or composition of the invention may be in the L-form or the D-form, usually in the L-form.

The proteineceous matter may comprise one or more proteins, which protein(s) or part thereof may have been modified, in particular by (partial) hydrolysis, usually to the extent that up to 20% of the protein is hydrolysed to free amino acids, preferably to the extent that up to 10% of the protein is hydrolysed to free amino acids. An advantage of (partially) hydrolysed protein is an advantageous amino-acid release behaviour, when enterally administered.

The peptide content (oligopeptide, polypeptide, protein) based on proteinaceous matter is usually at least 50 wt %, at least 60 wt %, or at least 75. The wt % of peptide, based on proteinaceous matter, is usually 99.5 wt % or less, preferably up 94 wt % or less. An advantage of a composition wherein the peptide content is high (≥50 wt %) is that the taste, or another organoleptic property of the composition, usually is appreciated better when consumed (orally). Further, the uptake of amino acids by the body may be more gradual.

The proteinaceaous matter preferably comprises at least one protein having at least 9 g of leucine per 100 g amino acids. The proteinaceous matter (providing leucine) preferably comprises at least one protein selected from the group of whey proteins, casein, caseinate, soy proteins and wheat proteins, preferably from the group of whey proteins and casein.

With whey proteins are meant globular proteins that can be isolated from whey. In particular, globular whey proteins can be selected from beta-lactoglobulin, alpha-lactalbumin and serum albumin, including mixtures thereof. Examples of mixtures that comprise whey proteins are whey isolate and whey concentrate.

In an embodiment, the proteinaceous matter comprises whey protein, in particular at least 10 wt. % based upon the proteinaceous matter, preferably at least 15 wt. % based upon the proteinaceous matter. Usually, the whey protein fraction is 50 wt. % or less based on proteinaceous matter, in particular 40 wt. % or less based on proteinaceous matter.

In particular in case of a liquid composition, the concentration of denatured whey protein preferably does not exceed 35 wt. % based upon the proteinaceous matter. This is advantageous with respect to avoiding the risk of gelation during storage.

The presence of a whey protein may offer a number of advantages. The whey shows an advantageous release behaviour both in terms of release rate of the amino acids and the tendency to make the amino acids available for uptake by the body, essentially at the same time.

Advantageously, part of the whey protein is (partially) hydrolysed, in particular up to 50 wt % of the whey protein may be (slightly) hydrolysed, in particular 10-50 wt %.

As the source for whey proteins preferably a whey fraction is chosen comprising less that 20 wt % casein glycomacropeptide (GMP), more preferably less than 10 wt %.

The beta-lactoglobulin content preferably is larger than 40 wt %, more preferably 46-80 wt %. This is advantageous because beta-lactoglobulin has a relatively high leucine content.

When used as intact protein, the casein preferably comprises a high concentration of beta casein, in particular more than 36 g/100 g casein, more in particular 38-70 g/100 g casein.

In an embodiment, all or part of the leucine is present in the form of free amino acids, a salt thereof or as a conjugate with a conjugating molecule other than a protein or peptide, which conjugate is capable of being split in the free amino acid (or salt thereof) and the conjugating compound under the influence of a bile constituent and/or a pancreas excretia in duodenum and/or the ileum. Preferably, the amount of leucine in such form, in particular in the form of a salt or the free form, is at least 1 wt. %, in particular at least 10 wt. %, more in particular at least 25 wt. %, based on total leucine. Preferably, the amount of leucine in such form, in particular in the form of a salt or the free form is up to 90 wt. %, in particular up to 75 wt. % more in particular up to 60wt. %.

A composition according to the invention usually comprises 15 g/kg leucine or more, preferably at least 25 g/kg leucine, in particular 30 to 70 g/kg leucine, more in particular 40 to 60 g/kg leucine, (including bound leucine) based on total weight of the macronutrients of the composition.

In a specific embodiment, the composition comprises at least 15 g/kg free leucine, based on total weight of proteinaceous matter, fat, carbohydrates plus dietary fibres, of the composition, in particular 22 to 35 g/kg freeleucine, more in particular 30 to 35 g/kg free leucine.

In terms of a daily dosage (for an adult subject, e.g. weighing 70 kg, in particular an adult human) leucine is usually to be administered in a dosage of at least 5 g/day, preferably at least 7 g/day. The dosage may in particular be up to 50 g/day, more in particular up to 35 g/day.

Usually, the amount of leucine as a percentage of total proteinaceaous matter is at least 12 wt. % Advantageously, the amount of leucine as a percentage of total proteinaceous matter is at least 15 wt. %, in particular at least 18 wt. %, more in particular at least 19 wt. %. Said amount is usually 30 wt. % or less, in particular 25 wt. % or less.

The combination or composition may further comprise one or more additional ingredients, in particular one or more ingredients selected from the group of digestible carbohydrates, indigestible carbohydrates and other dietary fibres, trace elements, minerals, vitamins, proteinaceous matter other than proteinaceous matter providing leucine (such as one or more free amino acids other than leucine), other lipids than the (poly)unsaturated fatty acid for treatment in accordance with the invention, and other typical additives for nutritional compositions, nutraceutical compositions or pharmaceutical compositions (such as antioxidants, flavourings, stabilising agent, or—in case of a pharmaceutical: a pharmaceutically acceptable carrier). Examples of additional ingredients are, e.g., described in WO2003/041701 (N.V. Nutricia) and WO2007/073178 (N.V. Nutricia). Examples of additional ingredients of which one or more may be present in a composition for use in accordance with the invention, in particular for a nutritional composition, in particular include sodium, potassium, chloride, fluoride, iodide, phosphorous, magnesium, vitamin A, vitamin D3, vitamin E, vitamin K, vitamin B1, vitamin B2, vitamin B3, vitamin B5, vitamin B6, folic acid, vitamin B12, biotin, vitamin C, lipoic acid, zinc, iron, copper, manganese, molybdenum selenium and chromium. Such components may be present in a concentration up to the daily recommended dose per daily serving.

In particular, good results have been achieved with a composition additionally comprising indigestible carbohydrate. There are indications that the presence of indigestible carbohydrate in combination with (ω3-poly) unsaturated fatty acid, in particular DHA and/or EPA, and leucine may have an additional advantageous effect on the calcium level in plasma, via a reduction of systemic inflammatory cytokine levels. Further, as illustrated by the examples, the presence of indigestible carbohydrate, in particular indigestible oligosaccharide may be beneficial with respect to immune function. In particular one or more indigestible oligosaccharides may be present, such as one or more oligosaccharides selected from the group of galactooligosaccharides (GOS) and fructooligosaccharides (FOS). With an oligosaccharide is meant a chain comprising 2 to 25 saccharide residues. If present, the indigestible carbohydrate content may in particular be about 20-70 g/kg, more in particular 40-60 g/kg, based on weight of the macronutrients. A daily dosage (for an adult, e.g. about 70 kg) may in particular be selected in the range of 2.5-15 g/day It is contemplated that dietary intervention with a low glycemic index diet is advantageous with respect to treatment of hypercalcaemia, reducing of bone mineral loss or avoiding a reduction in bone mineral density in a subject or the in vivo regulating of the blood plasma calcium homeostasis. Without being bound by theory, the inventors contemplate that a low glycemic index diet may affect the serum calcium levels in a positive manner because dietary intervention with a low glycemic index diet may have a positive effect on calcium serum levels, which effect may be associated to improved insulin sensitivity, as a result of intervention with the low glycemic index diet.

Accordingly, in a specific embodiment, the composition is a nutritional composition with a low glycemic index. In particular a composition with a glycemic index below 55, preferably below 45. In practice, the glycemic index will always be above zero, and usually be at least 1, in particular at least 5. Details on how to determine the glycemic index of a composition are provided in the Examples, herein below.

The skilled person will be able to formulate a composition with a relatively low glycemic index based on the information disclosed herein and common general knowledge. In particular, by increasing the percentage of carbohydrate that is digested more slowly than glucose or by increasing carbohydrates that provide less glucose moieties per weight than glucose, the glycemic index of a composition (under otherwise the same condition) is decreased. Preferred examples of carbohydrates which are digested more slowly than glucose are isomaltulose, fructose, galactose, lactose, trehalose. Next to that addition of fat and fibre can slow down gastric emptying. Moreover, fibres can form a physical barrier in the intestine, reducing absorption rate. Amino acids from protein can increase insulin release (especially leucine), and thereby increase glucose uptake by the cells. All these mechanisms can contribute to a reduction in glycemic index.

In a specific embodiment, the composition is a nutritional composition. With a nutritional composition is meant a composition that comprises naturally occurring components, preferably found in the food supply, that can be sold over the counter, as supplements, functional foods or food ingredients i.e. without a physician's or veterinarian's prescription. A nutritional composition may also be a medical food, intended for the dietary management of a disease or condition for mammals under the supervision of a physician or veterinarian.

A nutritional composition according to the invention may be in the form of a liquid, e.g. a drink, in the form of a semi-liquid, e.g. a yoghurt or a custard, in the form of a gel, e.g. jelly cake or in the form of a solid, e.g. a candy bar or an ice-cream.

In a specific embodiment the composition of the invention is a sip feed. In a more specific embodiment, the sip feed comprises 1.5-2.5 g/100 ml total leucine and 0.8-2 g/100 ml ω-3 polyunsaturated fatty acid.

In a specific embodiment the composition of the invention is a tube feed. In a more specific embodiment, the tube feed comprises 0.4-0.9 g/100 ml total leucine and 0.4-1 g/100 ml ω-3 polyunsaturated fatty acid.

In an embodiment, a liquid composition is prepared from a concentrate, e.g. from a liquid (e.g. with a viscosity of less than about 80 mPa·s), a semi-liquid (e.g. with a viscosity of more than about 80 mPa·s and less than about 400 mPa·s), a gel or a solid. For such preparation, water may be used to dilute the concentrate. In particular, such preparation occurs just before administration of the composition, e.g. in an instant-fashion.

A specific embodiment of the invention is a nutritional composition comprising proteinaceous matter, a lipid, and a digestible carbohydrate, wherein
  a) the proteinaceous matter content provides 18 to 50 en %, preferably 20 to 40 en %, more preferably 22 to 32 en % of the total composition;
  b) the lipid content provides 10 to 50 en %, preferably 20 to 40 en %, more preferably 25 to 35 en % of the total composition;
  c) the digestible carbohydrate content provides 20 to 70 en %, preferably 30 to 60 en %, more preferably 38 to 48 en % of the total composition.

The energetic value of a compound (en %) is based on the energy provided by the digestible part (in particular in a human) of the compound. In particular the energetic value is based on the contribution of proteinaceous matter, lipids and digestible carbohydrates, using the following calculation factors: 4 kcal/g for digestible carbohydrates and proteinaceous matter and 9 kcal/g for lipids.

The total energetic value of a liquid composition in accordance with the invention may be chosen within wide limits, e.g. from 0.2 to 4 kcal/ml. Usually the total energetic value is at least 0.3 kcal/ml, in particular at least 0.8 kcal/ml, more in particular at least 1.2 kcal/ml. Usually, the total energetic value is 3.0 kcal/ml or less, in particular 2.6 kcal/ml or less, more in particular 2.4 kcal/ml or less.

In a specific embodiment, a liquid composition according to the invention has an energetic value in the range of 0.3 to 3.0 kcal/ml, preferably of 0.8 to 2.6 kcal/ml, more preferably of 1.2 to 2.4 kcal/ml.

In a further specific embodiment, the liquid composition in accordance with the invention has an energetic value in the range of 0.2 to 1.0 kcal/ml, preferably of 0.4 to 0.9 kcal/ml. Such composition may in particular for use by elderly people.

Factors that play a role in determining a desirable energetic value include the ease of achieving a higher en % proteinaceous matter on the one hand and a fast emptying of the stomach (increasing anabolic response) on the other hand.

The combination or composition of the invention may be administered under the supervision of a medical specialist, or may be self-administered.

The composition or combination may be administered enterally (by tube feeding) or orally.

The invention will now be illustrated on the basis of the following examples.

EXAMPLES

Example 1

Formulation Example Sip Feed

TABLE 1

Nutritional composition sip feed

| | preferred range (g/100 ml) | specific formulation (g/100 ml |
|---|---|---|
| proteinaceous matter | 9-12 | 10.1 |
| containing total leucine | 1.5-2.5 | 1.95 |
| of which free leucine | 0.9-1.5 | 1.1 |
| carbohydrates (digestible) | 10-25 | 17.4 |
| fat | 2-6 | 5.3 |
| of which unsaturated | 2-6 | 4.2 |
| of which ω3-PUFA | 0.8-2 | 1.1 |
| dietary fibre (soluble) | 1-4 | 2 |

Example 2

Formulation Example Tube Feed

TABLE 2

Nutritional composition tube feed

| | preferred range (g/100 ml) | specific formulation (g/100 ml) |
|---|---|---|
| proteinaceous matter | 6-10 | 7.8 |
| containing total leucine | 1.0-2.0 | 1.5 |
| of which free leucine | 0.4-0.9 | 0.8 |
| carbohydrates (digestible) | 10-25 | 17 |
| fat | 2-6 | 5.4 |
| of which unsaturated | 2-6 | 4.5 |
| of which ω3-PUFA | 0.4-1 | 0.8 |
| dietary fibre | 1-4 | 1.5 |

Example 3

Test Results

Materials and Methods

Animals

Male CD2F 1 mice at 6-7 weeks of age, (BALB/c×DBA/2, Harlan/Charles River the Netherlands) were individually housed in a climate-controlled room (12:12 dark-light cycle with a constant room temperature of 21±1° C.). After acclimatization for one week mice were divided into weight-matched groups: (1) control receiving control chow, (2) tumour-bearing receiving control chow, and (3) tumour-bearing receiving experimental diets. Data shown are derived from the combination of several experimental runs with identical animal characteristics and experimental procedures (unless stated otherwise) and differ only in the experimental diets used. All experimental procedures were approved by the Animal Ethical Committee (DEC consult, Bilthoven, The Netherlands) and complied with the principles of good laboratory animal care.

Experimental Diets (Categories A and B Experiments)

Experiments are divided in: (A) experiments designed to test the effect of single or combinations of nutritional components (addition of free leucine (leu), ω-3 polyunsaturated fatty acid (from fish oil) (fo)), or the combination thereof added to the background diet (AIN93-M with high protein (151 g casein/kg)) and supplied as pellets; (B) experiments designed to test the effect of a complex nutritional combination that resembles the composition of an upgrade of FortiCare (Nutricia Advanced Medical Nutrition, NL) and comprises all individual components tested in (A), and differing in macronutrient composition from AIN-93 to achieve a more humanized Western-type diet, supplied as a dough for product technical reasons.

The AIN93-M high protein control diet in the experiments in which the effect of single ingredients was tested, contained per kg feed: 151 g protein (100% casein), 702 g carbohydrates and 40 g fat (100% soy oil) (Research Diet Services, Wijk bij Duurstede, the Netherlands). Experimental diets in this category were adjusted to control diets by partly replacing the carbohydrates and/or soy oil by leucine (151 g casein/kg and 16 g leucine/kg feed; leu), fish oil (151 g casein/kg and 22 g fish oil/kg feed; fo), or leucine and fish oil (151 g casein/kg, 16 g leucine/kg and 22 g fish oil/kg food; leu+fo). The 22 g fish oil contained 6.9 g EPA and 3.1 g DHA resulting in a EPA:DHA ratio of 2.2:1.

In the experiment in which the total combination of high protein, leucine, ω-3 polyunsaturated fatty acid (from fish oil) and oligosaccharides was tested, the control diet contained per kg feed 126 g protein (casein), 53 g fat (corn oil), and 699 g carbohydrates. The iso-caloric experimental diet (further referred to as Specific Nutritional Composition; SNC) contained per kg feed: 210 g protein (189 g intact protein of which 68% casein and 32% whey and 21 g free leucine), 53 g fat (20,1 g corn oil, 10,2 g canola oil, and 22,2 g fish oil), 561 g carbohydrates, 18 g galacto-oligosaccharides and 2 g fructo-oligosaccharides.

Tumour Model

Murine C-26 adenocarcinoma cells were cultured in vitro with RPMI 1640 supplemented with 5% fetal calf serum and 1% penicillin-streptomycin (31). Tumour cells were trypsinized in a sub-confluent state and, after washing, suspended in Hanks' balanced salt solution (HBSS) at a concentration of $2.5 \times 10^6$ cells·mL$^{-1}$. Under general anaesthesia (isoflurane/N$_2$O/O$_2$), tumour cells ($5 \times 10^5$ cells in 0.2 mL) were inoculated subcutaneously into the right inguinal flank of the mice. Control (C) animals received a sham injection with 0.2 mL HBSS.

Experimental Protocol

Following inoculation of tumour cells or HBSS, body mass, food intake and tumour size (length and width) were measured three times a week. Only in the category B experiment, daily activity in the home cage was monitored. In all experiments, animals were anaesthetized and weighted at day 20 after tumour inoculation. Skeletal muscles (e.g. m. Tibialis Anterior (mTA), m. Gastrocnemius (mG), m. Extensor Digitorum Longus (mEDL) and M. Soleus (mS)), the tumour, spleen, kidneys, liver, epididymal fat, thymus, lungs and heart were dissected and weighed. Carcass mass was calculated by subtracting tumour mass from body mass. In addition, muscle function was tested ex vivo in the category B experiment.

Assessment of Daily Activity

Physical activity was monitored continuously (24 h) during the 20-day study period starting at day 2, using activity sensors (dual technology detector DUO 240, Visonic; adapted by R. Visser, NIN, Amsterdam, The Netherlands) that translated individual changes in the infrared pattern caused by movements of the animals into arbitrary activity counts. Sensors were mounted above the home cages and were connected via input ports and interface to a computer equipped with MED-PC IV software for data collection (MED associates, St. Albans, Vt.). Activity was expressed in counts per hour (both for the total 24-h period, the dark period (active period, mice being nocturnal animals) and the light period (inactive period)). Activity was calculated for each mouse separately and was expressed relative to its own total activity on day 2, to correct for differences in the individual sensitivity of sensors. The activities of two subsequent days were averaged, to dampen the day to day variability. In order to determine changes in activity pattern throughout the experiment, hourly and dark-light activity were expressed as percentage of total daily activity and translated into an actogram.

Assessment of Muscular Functionality

Contractile characteristics of the right EDL muscle were assessed ex vivo, as described previously (van Norren, K., Kegler, D., Argiles, J. M., Luiking, Y., Gorselink, M., Laviano, A., Arts, K., Faber, J., Jansen, H., van der Beek, E. M. & van Helvoort, A. (2009): Dietary supplementation with a specific combination of high protein, leucine, and fish oil improves muscle function and daily activity in tumour-bearing cachectic mice. Br J Cancer., 100, 713-22.).

Briefly, muscles were allowed to stabilize in the organ bath for 30 min, after which optimal stimulation current and strength were determined. Then force-frequency characteristics (10 to 167 Hz, 250 ms) were determined and after replenishing the organ buffer and a resting period of 5 min, muscles were subjected to an exercise protocol (83 Hz, 250 ms every 1000 ms). This protocol represents a moderate load, comparable with normal daily activity. At the frequency used, complete tetanus of the muscle is reached. Isometric force signals of the force-frequency curve were analyzed for maximal and total force and for maximal contraction and relaxation velocity.

Statistics

All data are expressed as means±SEM. Statistical analyses were performed using SPSS 15.0 (SPSS Benelux, Gorinchem, the Netherlands). In experiment A different batches of animals were used, therefore, for all parameters it was defined that combination of data was allowed if no interaction between groups and experiments were present. Body composition data, tumour and organ masses on day 20 were compared between groups with analysis of variance (ANOVA) and post-hoc LSD. Differences were considered significant at a p value below $\alpha/k$; in which $\alpha=10\%$ and k=amount of comparisons. For exp A the p value had to be below 0.02; for experiment B the p value had to be below 0.05. Data on food intake, body weight, daily activity, and muscle function that were monitored during the 20 days after inoculation were analyzed by repeated measures ANOVA. To further discriminate the differences between groups, the differences or deltas from the first measurement in the range were calculated. These deltas were compared between groups using ANOVA, with post-hoc LSD for pair-wise comparison between groups. For skeletal muscle function, data of first measurement at day 20 were not similar between groups, therefore further discrimination was performed in a per point analysis ANOVA. Differences were considered significant at a two tailed p<0.05.

Results

Figure 1A:
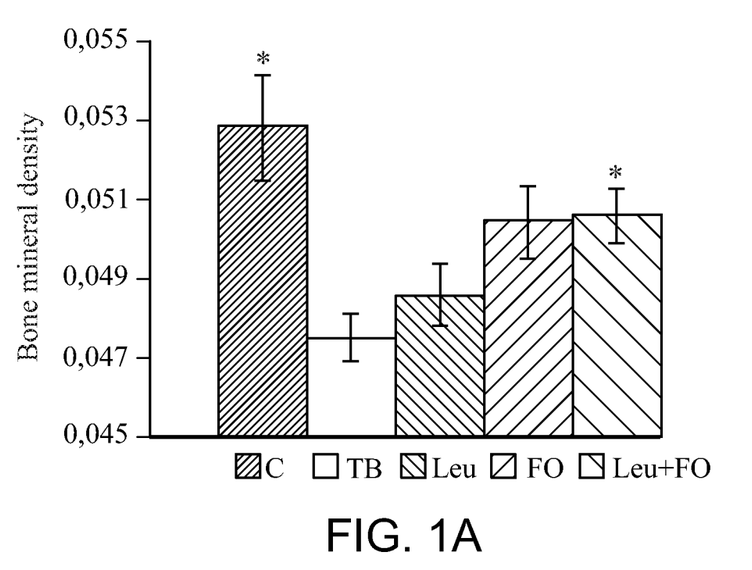
FIG. 1A shows the effect of leucine, ω-3 polyunsaturated fatty acid (from fish oil) or the combination thereof on bone mineral density. C=control, TB=tumour-bearing mice receiving control diet, leu=leucine, fo=fish oil.
Figure 1B:
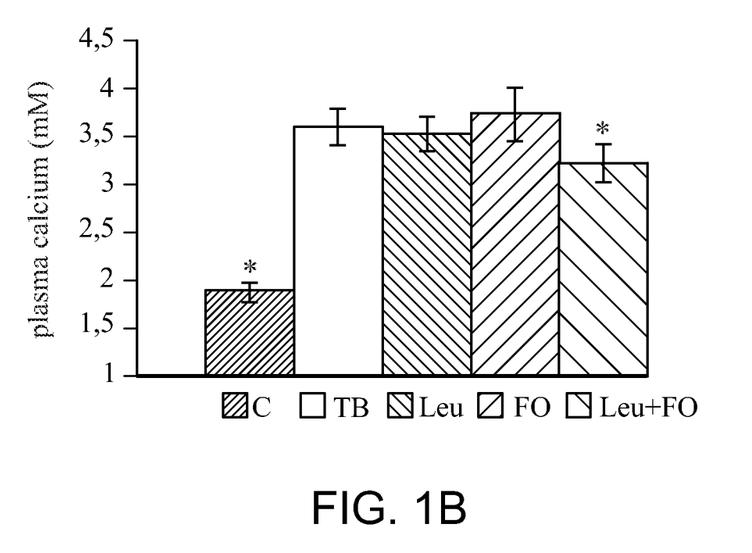
FIG. 1B shows the effect of leucine, ω-3 polyunsaturated fatty acid (from fish oil) or the combination thereof on plasma calcium levels. C=control, TB=tumour-bearing mice receiving control diet, leu=leucine, fo=fish oil.
Figure 2:
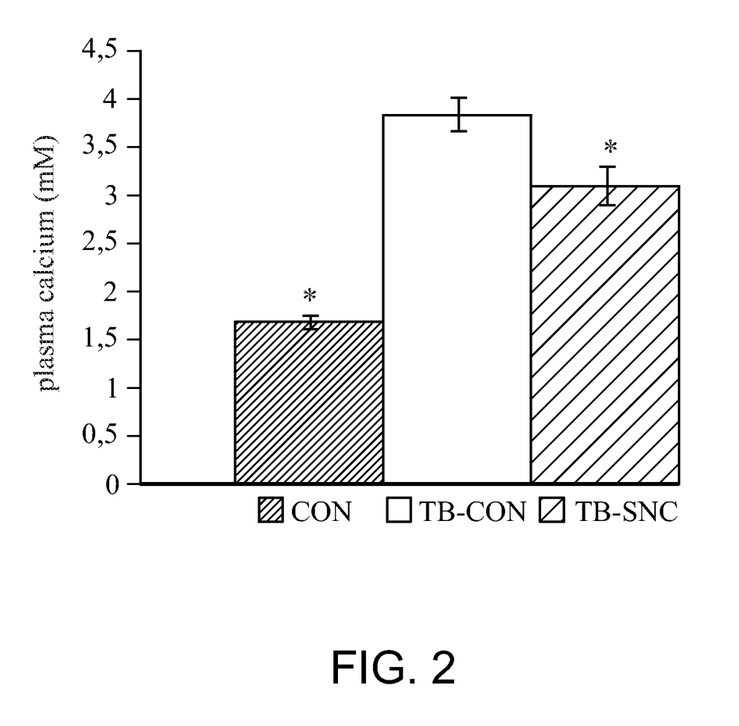
FIG. 2 shows the effect of the total specific combination of leucine, (part bound in protein, part in free form) ω-3 polyunsaturated fatty acid (from fish oil) and oligosaccharides on plasma calcium levels. CON=mice receiving control diet B, TB-CON=tumour-bearing mice receiving control diet B, TB-SNC=tumour-bearing mice receiving the specific nutritional combination.

Bone mineral density was decreased in tumour-bearing mice (TB) compared to control mice (C) (FIG. 1A). Addition of either leucine or ω-3 polyunsaturated fatty acid (from fish oil) did not result in significant changes compared to TB. However, the combination of ω-3 polyunsaturated fatty acid and leucine, resulted in a significant increase of bone mineral density compared to TB. The presence of a tumour induced an increase in plasma calcium levels of about 75% (FIG. 1B). Supplementation with single ingredients (TB-leu or TB-fo) had no effect on calcium levels of the tumour bearing animals. The combination of leucine and ω-3 polyunsaturated fatty acid however, resulted in a significant reduction of plasma calcium levels. Similar reductions in plasma levels were found in animals supplemented with a complete nutritional combination of fish oil, leucine and oligosaccharides (experiment B) (FIG. 2).

Figure 3:
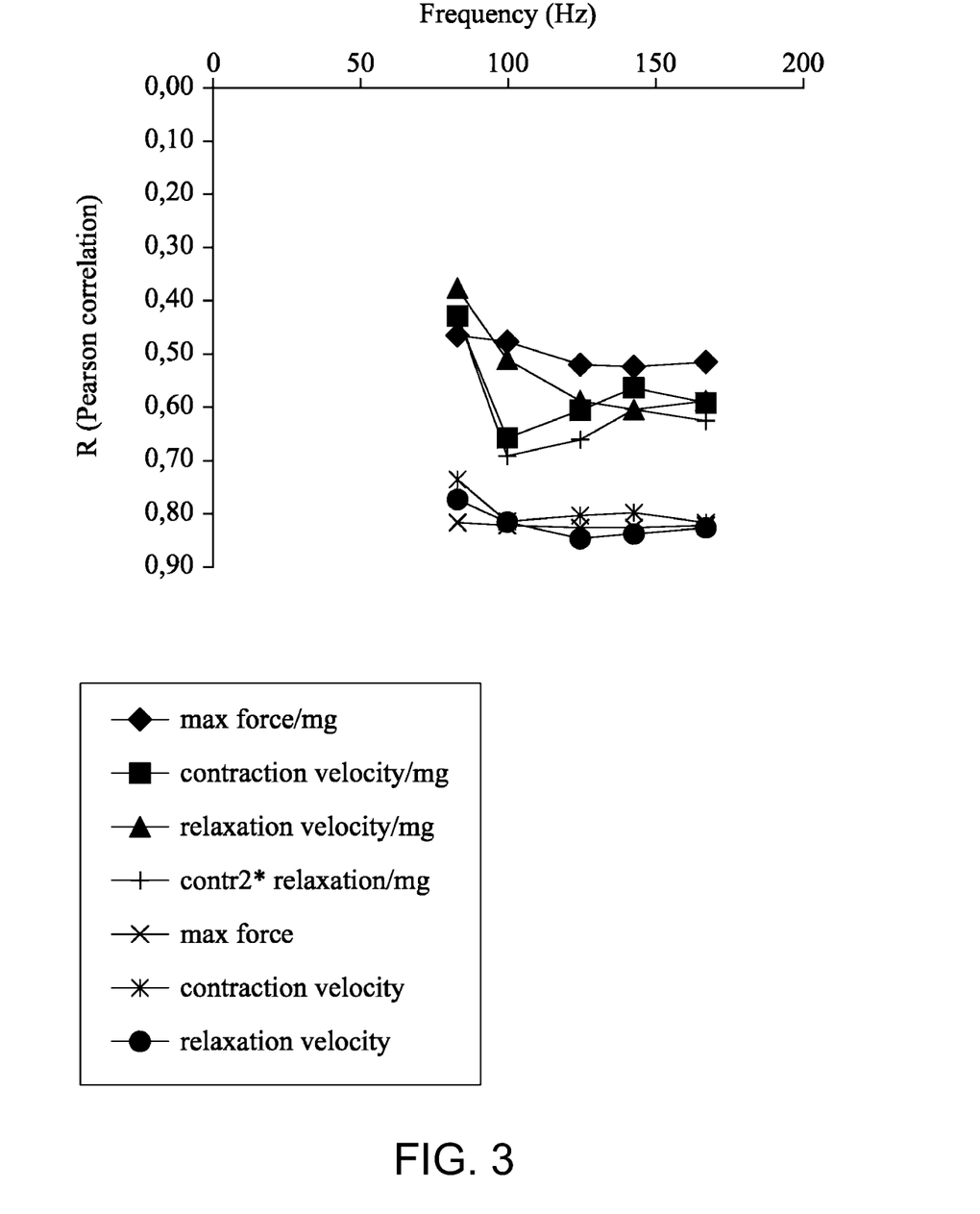
FIG. 3 shows correlations of muscle function parameters with calcium levels. Data labels represent a Pearson correlation factor R with $p<0.05$. One data point represented as an open label (relaxation velocity/mg, 83 Hz) had a p value of 0.057. Contr2*relaxation/mg=the square root of the contraction time corrected for muscle mass times the maximal relaxation velocity corrected for muscle mass.

The muscles from control animals showed a higher maximal force, maximal contraction velocity and maximal relaxation velocity when compared to TB control mice. The specific nutritional combination of ω-3 polyunsaturated fatty acid, leucine (part free leucine, part bound in protein) and oligosaccharides corrected this in part both for muscle mass dependent as for muscle mass independent differences. The same experiment was used to study in more detail the correlation of calcium levels with muscle performance parameters. For all frequencies at which tetanus could be obtained (>83 Hz), muscle function parameters (maximal force, maximal contraction velocity and maximal relaxation velocity) correlated negatively with the calcium levels (R below −0.7 and p<0.05) (FIG. 3). When the muscle function parameters, maximal force, maximal contraction velocity and maximal relaxation velocity were corrected for muscle mass, negative correlations remained (R between −0.4 and −0.7) (FIG. 3).

Figure 4:
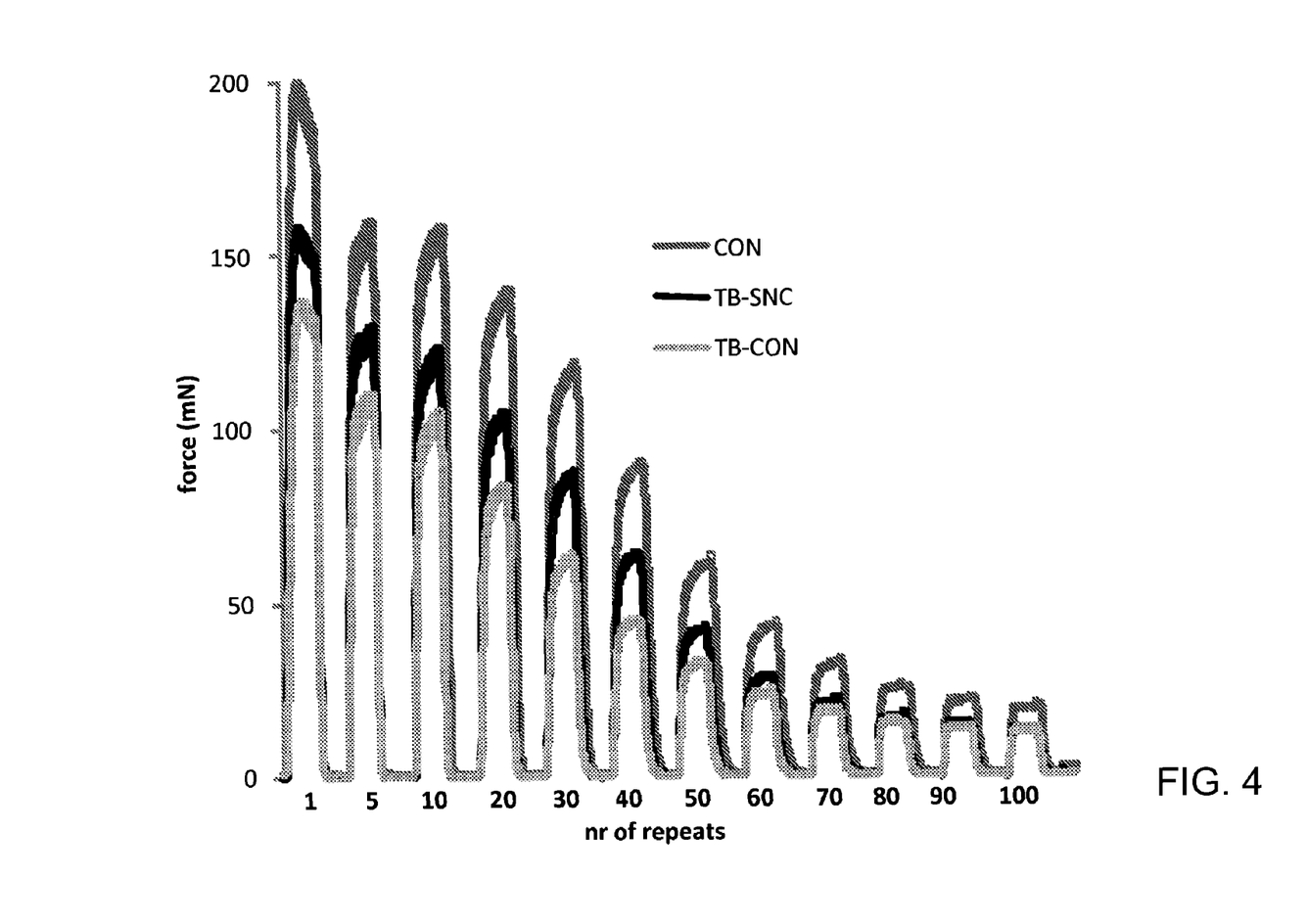
FIG. 4 shows representative examples of individual force curves (the curve of animals with max force data best fitting to the curve of the mean). CON=mice receiving control diet B, TB-CON=tumour-bearing mice receiving control diet B, TB-SNC=tumour-bearing mice receiving the specific nutritional combination.

Repetitive stimulations at 83 Hz, mimicking a moderate exercise, induced loss of maximal force in all three groups. Loss in force was more severe in the TB-CON group compared to the CON group. The specialized nutritional combination partly normalized this. In FIG. 4 representative examples (the curve closest to the mean curve) of the complete force curves obtained during exercise are shown. For all curves the pattern of the peaks changes in the first 5 repeats. The time point at which max force is obtained changes to the end of the pulse when compared to the first repeat.

Figure 5:
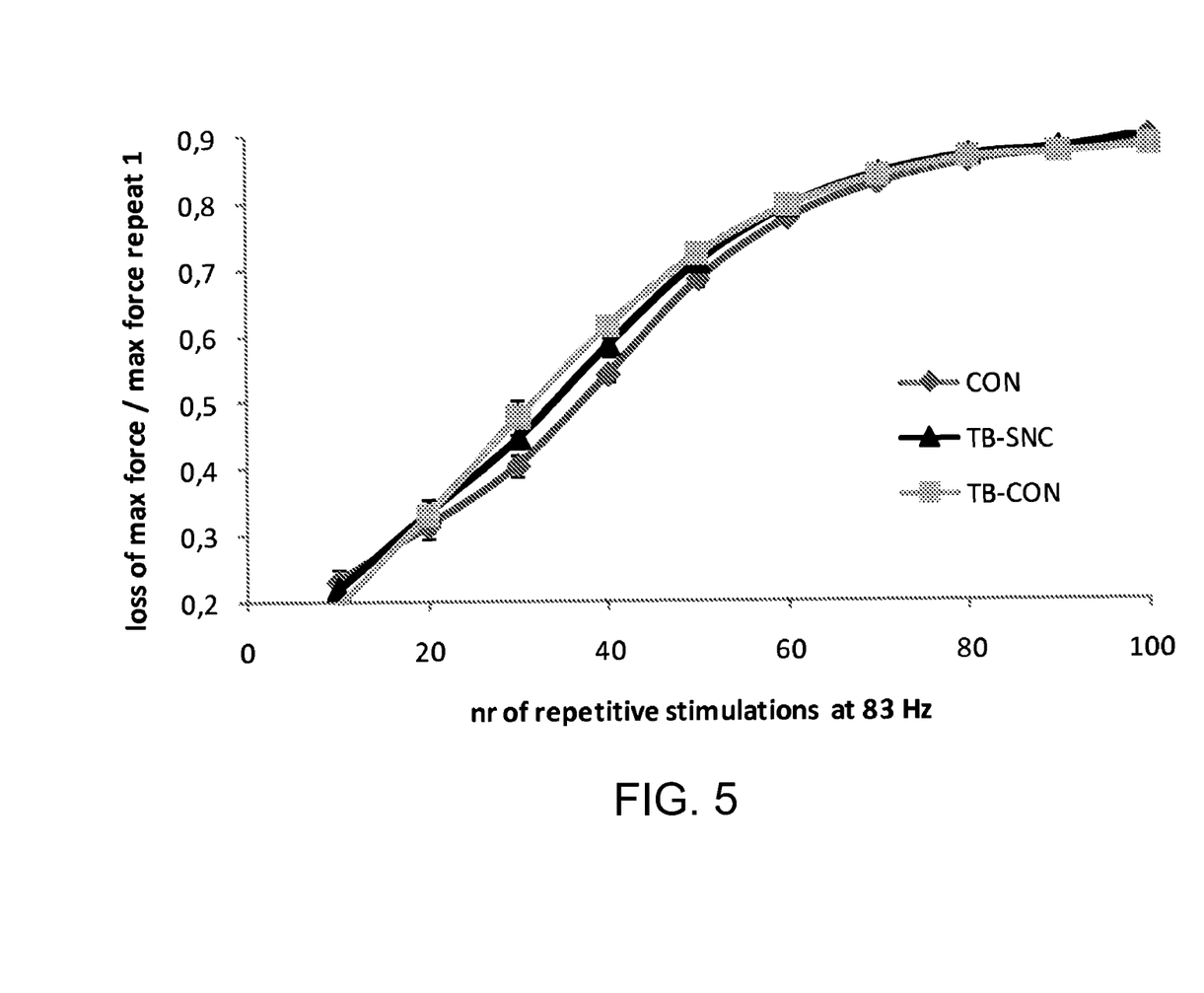
FIG. 5 shows measurement of fatigue during repetitive stimulation, a model mimicking exercise. Data presented are: cumulative loss per 10 repeats in muscle corrected maximal force divided by the muscle mass corrected maximal force at repeat 1.
Figure 6:
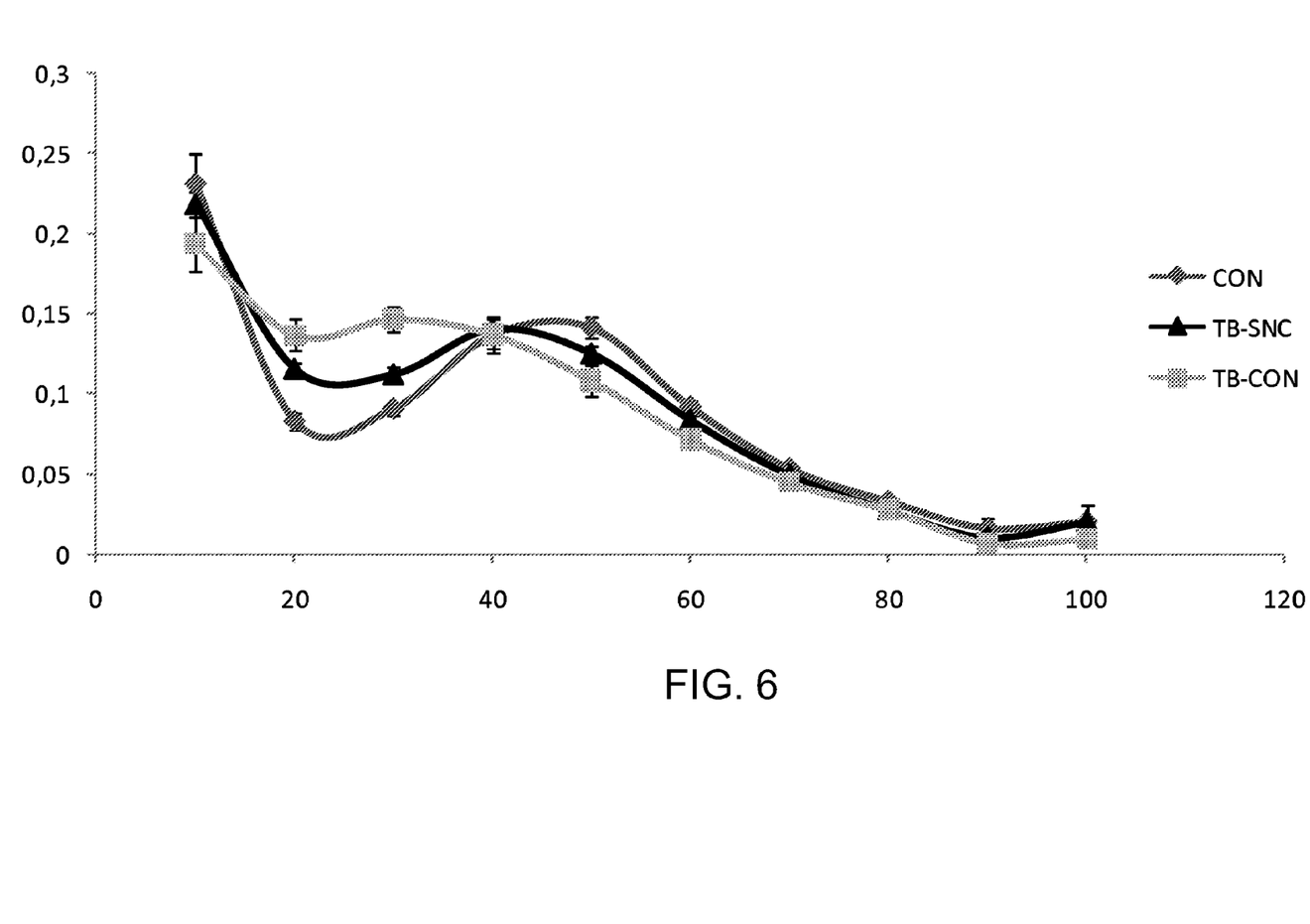
FIG. 6 shows distribution of relative loss in maximal force during repetitive stimulation, a model mimicking exercise. Data presented are: muscle corrected maximal force at time repeat x—maximal force at time repeat (x-20) divided by the muscle mass corrected maximal force at repeat 1. CON=mice receiving control diet B, TB-CON=tumour-bearing mice receiving control diet B, TB-SNC=tumour-bearing

To obtain a better insight in the resistance of the muscle to fatigue, relative changes in maximal force were calculated. If data were presented relatively to the maximal force at start of the exercise (corrected for muscle mass), the first 20 repeats resulted in a similar cumulative loss of maximal force and also at 80 repeats the cumulative relative loss of maximal force was the same (FIG. 5). The control mice however, showed less cumulative loss of max force between 20 and 50 repeats than the tumour-bearing mice. The TB-SNC mice showed a tendency to an intermediate loss of relative maximal force. This difference in distribution pattern of relative maximal forces becomes more prominent when expressed as relative loss per 10 repeats (FIG. 6). Both the curves of CON and TB-SNC were significantly different from TB-CON from repeats 30-70. The data also showing less relative loss of maximal force in the first 40 repeats.

Figure 7:
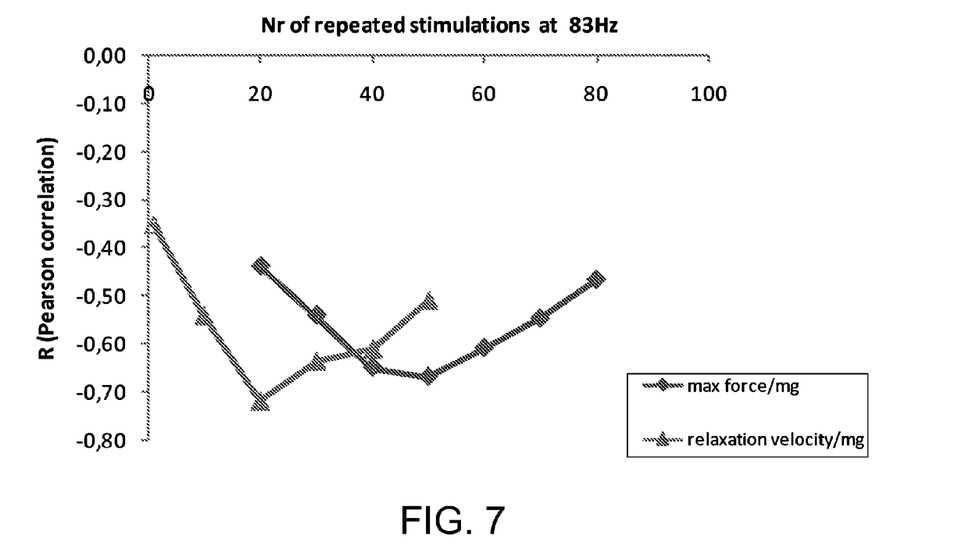
FIG. 7 shows correlations of muscle function parameters during exercise with calcium levels. Data labels represent a Pearson correlation factor R with $p<0.05$. Two data points represented as open labels (relaxation velocity/mg and ftr both at 83 Hz) had a p value of 0.077 and 0.074 respectively.

To further elucidate the relation between muscle function during repetitive stimulation and calcium, it was determined which muscle function parameter correlated best with calcium levels throughout the complete repetitive stimulation. In FIG. 7, the muscle function parameters are shown that show a correlation factor of less than −0.35 and p<0.05 for at least 50 repeats. For the first 40 repeats, muscle mass corrected relaxation velocity showed the most stringent negative correlation with calcium levels. From 40-80 repeats, muscle mass corrected maximal force correlated best negatively with the calcium levels. When a quadratic set of calcium data was used, muscle mass correlation factors were similar.

Figure 8:
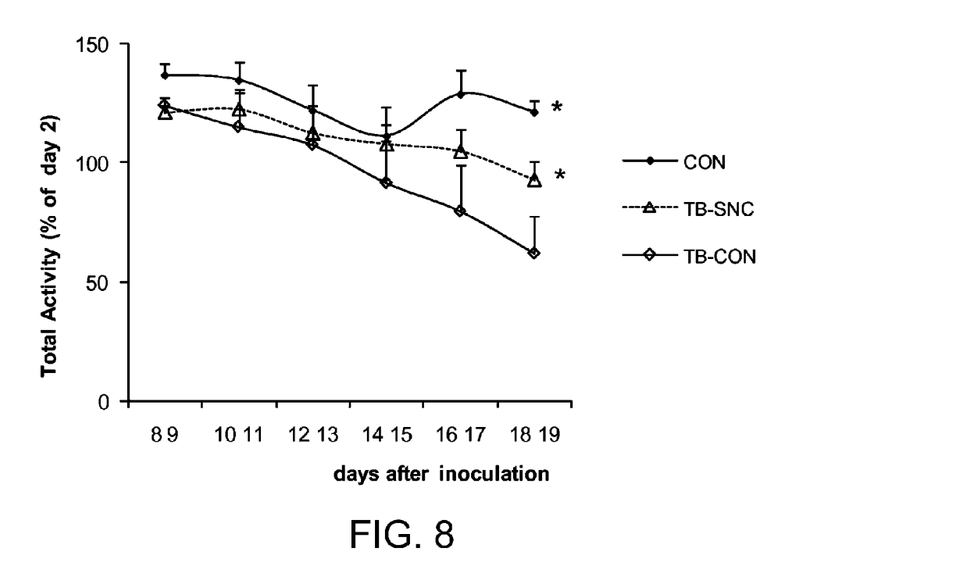
FIG. 8 shows daily activity per mouse when compared to activity per mouse at day 2. CON=mice receiving control diet B, TB-CON=tumour-bearing mice receiving control diet B, TB-SNC=tumour-bearing mice receiving the specific nutritional combination.

The daily activity declined in the TB-CON group, which was partly normalized in the TB-SNC group compared to CON (FIG. 8). CON and TB-SNC were significantly different from TB-CON. Total daily activity negatively correlated with calcium levels (Table 3B). The activity in the dark (active) period correlated even better with the calcium concentrations. There was no correlation between calcium levels and the activity in the light (dormant) period. Quadratic calcium levels correlated slightly less with activity parameters.

Discussion

The results indicate that a partial normalization of calcium levels, was only reached when leucine and ω-3 polyunsaturated fatty acid (of fish oil) were combined.

Further, this combination was suitable to partly normalize the distribution of loss in relative maximal force.

In particular, an improvement in daily activity (nocturnal in the test-animals) was observed compared to a control group. Moreover, calcium concentrations correlated with the daily activity, and especially with the activity in the dark (active) period, again, suggesting that incidence of fatigue might be reduced in accordance with the invention.

Both the data from repetitive stimulation, mimicking an exercise, and the data from single stimulations at different frequencies suggest that calcium levels correlate in a nearly linear way to muscle performance. Therefore, prevention or treatment of elevation of calcium levels with nutritional interventions might be an option for patients with or at risk of hypercalcaemia to contribute to maintenance of quality of life of the patient.

Example 4

Glycemic Index determination

Definition

The glycemic index (GI) of a carbohydrate provides a measure of its ability to raise postprandial glucose concentrations. High GI foods give higher postprandial blood glucose levels than those with a low GI. The GI of a carbohydrate also predicts the insulin response to that food.

The GI of a carbohydrate is calculated by assessing a 25 g two-hour glycaemic response with that of a subsequent 25 g carbohydrate standard glucose:

GI equals 'Incremental area under blood glucose response curve for a test food containing 25 g of carbohydrate' divided by 'Corresponding area after equivalent carbohydrate portion of glucose'

Glycaemic Index Methodology

Available carbohydrate is defined for GI testing purposes as: Total carbohydrate minus the indigestible carbohydrates (soluble and insoluble) that are from a physiological point dietary fibres (e.g. inulin, FOS, type 3 resistant starch).

The samples provided should be representative of the product as available to the consumer in the market place.

All foods submitted for testing are tested in vivo, that is, in 10 human subjects consuming amounts containing the equivalent of 25 g available carbohydrate. They are healthy subjects with no chronic diseases, diabetes or glucose impairment. Subjects have a BMI between 18.5-27 kg/m².

Reference food: The reference food is 25 g glucose powder dissolved in 250 mls water. Each person tests the reference food at least twice.

Test foods: The test foods are prepared according to manufacturer's instructions, representing the food as normally consumed. The test foods are consumed once only on separate occasions as a portion providing 25 g of available carbohydrate, defined as above.

Protocol Subjects: Subjects are tested in the morning after a 10-12 h overnight fast. Two fasting blood samples are taken (−5 & 0) 5 minutes apart after which subjects consume the test meal or reference food at an even rate over 15 minutes. Further blood samples are taken at 15, 30, 45, 60, 90 and 120 minutes after the beginning of the meal. The test meal and reference food should be consumed with a 250 mls drink of water. This remains constant for each of the tests in the series.

24 hrs prior to GI test: The day before each session, subjects refrain from drinking alcohol and avoid unusual levels of exercise and food intake. Subjects must have an evening meal based on a carbohydrate-rich food, such as rice, pasta, bread, potatoes and not too much fat. This meal should not include beans, pulses or legumes (to avoid a second meal effect the next morning). It is important that they eat dinner and not fast for more than 18 hours. Subjects are asked to be in a similar state each time they come in for a session. After they have eaten their evening meal, subjects fast for at least 10 hours overnight before the start of their test session the next morning. They can drink only water during the fasting period.

Blood sampling: Blood will be obtained by finger pricking

Blood is collected without clotting inhibitors (heparin, EDTA).

Glucose assay: Whole capillary blood or is measured by an automatic glucose analyzer. In this case, Hemocue glucose analysers are used.

Data analysis: The incremental area under the blood glucose response curve (iAUC), ignoring area beneath the baseline, is calculated geometrically as follows:

For times t0, t1, . . . to the blood glucose concentrations are G0, G1, . . . Gn, respectively:

$$iAUC = \sum_{n}^{x=1} Ax$$

wherein Ax=the AUC for the xth time interval (i.e. between tx−1 and tx).

For the first time interval (i.e. x=1): if G1>G0, A1=(G1−G0)×(t1−t0)/2 otherwise, A1=0

For the other time intervals (i.e. x>1)

if Gx≥G0 and Gx−1≥G0, Ax={[(Gx−G0)/2]+(Gx−1−G0)/2}×(tx−tx−1)

if Gx>G0 and Gx−1<G0, Ax=[(Gx−G0)²/(Gx−Gx−1)]×(tx−tx−1)/2 if Gx<G0 and Gx−1>G0, Ax=[(Gx−1−G0)²/(Gx−1−Gx)]×(tx−tx−1)/2 if Gx≤G0 and Gx−1<G0, Ax=0

GI calculation: In individual subjects, the GI value is the iAUC for each food expressed as a percentage of the mean iAUC of the two reference foods (glucose). The GI of the test food is the mean GI±SEM of the 10 subjects.

Up to two outliers (an outlier is an individual whose GI differs from the mean by more than two SD) may be excluded from the data set. SEM should be within 20% of the mean.

The invention claimed is:

1. A method for the therapeutic treatment of hypercalcaemia in an individual, comprising administering to the individual a composition comprising a leucine source and an ω-3 unsaturated fatty acid source providing an ω-3 polyunsaturated fatty acid selected from the group consisting of eicosapentaenoic acid, docosahexaenoic acid, eicosatetraenoic acid and docosapentaenoic acid, wherein the individual is a subject suffering from a cancer, and wherein the composition further includes at least one indigestible oligosaccharide.

2. The method of claim 1, wherein fatigue is reduced in the individual.

3. The method of claim 1, wherein the cancer is selected from the group consisting of lung cancer, breast cancer, kidney cancer, multiple myeloma cancer, and head and neck cancer.

4. The method of claim 1, wherein the composition is used in the treatment of excessive calcium release from bone and/or skeletal muscle; or in the treatment of excessive calcium accumulation due to kidney failure or hyperparathyroidism.

5. The method of claim 1, wherein the individual is a patient subjected to radiotherapy or chemotherapy.

6. The method of claim 1, wherein the leucine source comprises at least one compound selected from the group consisting of leucine in the form of a free acid (including its zwitter ionic state), leucine salts, peptides comprising one or more leucine units, proteins comprising one or more leucine units, and conjugates of leucine with a conjugating compound other than an amino acid, a protein, or a peptide, which conjugate is capable of being split into the free amino acid or salt thereof.

7. The method of claim 1, wherein the leucine source comprises at least 12 wt % of leucine based on total proteinaceous matter.

8. The method of claim 7, wherein the leucine source comprises at least 15 wt % of leucine based on total proteinaceous matter.

9. The method of claim 8, wherein the leucine source comprises more than 18 wt % of leucine based on total proteinaceous matter.

10. The method of claim 1, wherein the at least one indigestable oligosaccharide is an galactooligosaccharide, or fructooligosaccharide.

11. The method of claim 1, wherein the composition comprises at least 15 g/kg total leucine, based on total weight of proteinaceous matter, fat, carbohydrates plus dietary fibres, of the composition.

12. The method of claim 11, wherein the composition comprises 30 to 70 g/kg leucine.

13. The method of claim 12, wherein the composition comprises 40 to 60 g/kg leucine.

14. The method of claim 1, wherein the composition, has an ω-3 polyunsaturated fatty acid content, based on total lipids, of at least 12 wt %.

15. The method of claim 14, wherein the composition, has an ω-3 polyunsaturated fatty acid content, based on total lipids, of 18 wt % or more.

16. The method of claim 1, wherein the composition comprises a marine oil or a fraction thereof, which marine oil or fraction thereof provides at least 70 wt % of the total of ω-3 polyunsaturated fatty acids in the composition.

17. The method of claim 1, wherein the composition comprises a carbohydrate and is a nutritional composition having a glycemic index of less than 55.

18. The method of claim 1, wherein the individual is a human.

19. A method for the therapeutic treatment of hypercalcaemia in an individual, comprising administering to the individual a composition comprising a leucine source and an ω-3 unsaturated fatty acid source providing an ω-3 polyunsaturated fatty acid selected from the group consisting of eicosapentaenoic acid, docosahexaenoic acid, eicosatetraenoic acid and docosapentaenoic acid, wherein the individual is a subject suffering from a cancer and, wherein the composition comprises at least 15 g/kg free leucine, based on total weight of proteinaceous matter, fat, carbohydrates plus dietary fibres, of the composition.

20. The method of claim 19, wherein the composition comprises 22 to 35 g/kg free leucine, based on total weight of proteinaceous matter, fat, carbohydrates plus dietary fibres, of the composition.

21. A method for the prophylactic or therapeutic treatment of hypercalcaemia in an individual comprising administering to the individual a nutritional composition comprising proteinaceous matter, a lipid, and a digestible carbohydrate, wherein
  a) the proteinaceous matter content provides 18 to 50 en % of the total composition; the proteinaceous matter providing a leucine source providing at least 15 g/kg leucine, based on total weight of proteinaceous matter, fat, carbohydrates, plus fibers of the composition, a first part of the leucine being in a free form, a second part provided by whey protein,
  b) the lipid content provides 10 to 50 en % of the total composition; the lipid comprising and an ω-3 polyunsaturated fatty acid source providing eicosapentaenoic acid and docosahexaenoic acid, wherein the ω-3 polyunsaturated fatty acid content is at least 15 g/kg,
  c) the digestible carbohydrate content provides 20 to 70 en %, of the total composition.
  d) an indigestible carbohydrate selected from the group of galactooligosaccharides (GOS) and fructooligosaccharides (FOS), the composition having a glycemic index of less than 55.

22. The method of claim 21, wherein the individual to which the nutritional composition is administered is a patient suffering from a neoplasm.

23. The method of claim 22, wherein the neoplasm is a lung cancer, breast cancer, kidney cancer, multiple myeloma cancer or head and neck cancer.

24. The method of claim 21, wherein the individual to which the nutritional composition is administered has hypervitaminosis D.

25. The method of claim 21, wherein the individual to which the nutritional composition is administered has hyperparathyroidism.

26. The method of claim 21, wherein the individual to which the nutritional composition is administered has Paget's disease of the bone.

27. The method of claim 21, wherein the individual to which the nutritional composition is administered has renal failure.

28. The method of claim 21, wherein the individual to which the nutritional composition is administered is a prolongedly immobilized subject.

29. The method of claim 21, wherein the individual to which the nutritional composition is administered has aluminium, intoxication, vitamin A intoxication or intoxication with another substance that may result in hypercalcaemia, if not treated.

30. The method of claim 21, wherein the nutritional composition is administered to provide a long chain ω-3 polyunsaturated fatty acid dosage, of 3.5 g/day-25 g/day and to provide a leucine dosage of 5 g/day to 35 g/day.

31. The method of claim 21, wherein the individual to which the nutritional composition is administered is a patient suffering from a hematologic malignancy.

* * * * *